United States Patent
Reindel et al.

(10) Patent No.: US 10,156,590 B1
(45) Date of Patent: Dec. 18, 2018

(54) DIGITAL MULTIMETER

(71) Applicant: American Innovations, Ltd., Austin, TX (US)

(72) Inventors: Kenneth Alan Reindel, Broomfield, CO (US); Stephen Peter Jachim, Cedar Park, TX (US)

(73) Assignee: AMERICAN INNOVATIONS, LTD., Austin, TX (US)

( * ) Notice: Subject to any disclaimer, the term of this patent is extended or adjusted under 35 U.S.C. 154(b) by 327 days.

(21) Appl. No.: 14/879,915

(22) Filed: Oct. 9, 2015

(51) Int. Cl.
*G01R 15/12* (2006.01)
*G01R 19/25* (2006.01)
*G01N 27/04* (2006.01)
*G01N 17/04* (2006.01)

(52) U.S. Cl.
CPC ........... *G01R 15/125* (2013.01); *G01N 17/04* (2013.01); *G01N 27/04* (2013.01); *G01R 19/2506* (2013.01)

(58) Field of Classification Search
None
See application file for complete search history.

(56) References Cited

U.S. PATENT DOCUMENTS

| | | | | |
|---|---|---|---|---|
| 4,082,998 A * | 4/1978 | Marriott | ............... | G01R 19/255 324/111 |
| 5,343,404 A * | 8/1994 | Girgis | .................. | G01R 15/125 324/623 |
| 5,396,168 A * | 3/1995 | Heep | ..................... | G01R 15/125 324/115 |
| 6,259,482 B1 * | 7/2001 | Easley | .................. | H03G 7/007 348/484 |
| 2008/0111560 A1 * | 5/2008 | Regier | ................. | G01R 15/125 324/609 |
| 2009/0027042 A1 * | 1/2009 | Yao | ...................... | G01R 15/125 324/123 R |

\* cited by examiner

*Primary Examiner* — Melissa Koval
*Assistant Examiner* — Nasima Monsur
(74) *Attorney, Agent, or Firm* — Jackson Walker L.L.P.

(57) ABSTRACT

A digital multimeter receives a primary signal including a small amplitude DC component and an induced AC noise component with a magnitude exceeding a magnitude of the DC component. A 100 MΩ input resistor may couple an primary signal to signal processing circuitry that attenuates and filters the primary signal, convert a unipolar signal to a differential signal, and provide the differential output signal to an analog to digital converter. The multimeter may be configurable to couple any one or more of multiple available feedback paths to provide a plurality of available gain-bandwidth configurations. The multimeter may include a second input configurable with two or more feedback path impedances. The multimeter may include a second stage filter, shared by the primary and shunt inputs, that provides additional filtering and converts the signal to a differential signal. The second stage filter may support two or more available impedance configurations.

24 Claims, 4 Drawing Sheets

DIGITAL MULTIMETER

FIELD

Subject matter described herein emphasizes digital multimeters and, more particularly, digital multimeters suitable for measuring small amplitude DC voltages across high impedance circuits in electrically noisy and geographically remote environments.

BACKGROUND

The following brief description of a cathodic protection system illustrates an application and environment in which the measurement of a small DC voltage is equally challenging and necessary. Cathodic protection systems are designed to combat corrosion that inevitably occurs when metallic structures are located in contact with the soil or another electrolytic medium. The metallic structure is typically coated to retard corrosion. Coatings for large structures such as steel pipelines inevitably include or develop defects, voids, or "holidays" that expose the underlying metal to the medium. To address corrosion that would otherwise occur at a holiday, a cathodic protection (CP) system impresses an electrical current in opposition to a corrosion current that flows between the metallic structure and the electrolytic medium. An impressed current CP system includes an external DC power supply that biases the metallic structure relative to the electrolytic medium, changing the electrochemical state of the metallic structure and thereby preventing or slowing the corrosion process.

The voltage across the interface between the metallic structure and the electrolytic medium is a primary determinant of how well a CP system protects a pipeline or other structure against corrosion. For CP system applications in which the metallic structure is an underground steel pipeline and the electrolytic medium is the surrounding soil, the "pipe-to-soil" potential (PTSP), i.e., the potential across the interface between the pipe and soil, is a critical parameter. One rule of thumb commonly encountered in the cathodic protection industry suggests a pipe-to-soil potential more negative than −0.85 V.

Direct measurement of the PTSP not being generally feasible, the PTSP may be estimated by measuring the potential between the pipe and a reference electrode, e.g., a copper-copper sulfate electrode, located in proximity to the pipe itself. This technique, however, introduces an unwanted resistive element, corresponding to the soil between the pipe and the reference electrode, into the current path of the PTSP measurement circuit. An IR voltage drop across this resistive element represents a discrepancy between the measured potential and the actual PTSP. The magnitude of this discrepancy may be estimated by measuring a first voltage, referred to as the "on potential", while the CP system is operating and a second voltage, referred to as an "instant off potential", very soon after turning off the CP system under the assumption that the primary component of any difference between the on potential and the instant off potential is attributable to the elimination of the IR drop across the soil when the impressed current is terminated.

Cathodically protected structures may be located in proximity to one or more sources of time varying electromagnetic fields. Steel pipelines, for example, are frequently located beneath or in proximity to high power transmission lines. In such environments, the amplitude of the total noise, which may include thermal noise, noise induced by these transmission lines, and noise attributable to other sources, may exceed the amplitude of the signal-of-interest by multiple orders of magnitude, thereby making accurate estimates of the PTSP difficult to obtain.

BRIEF DESCRIPTION OF THE DRAWINGS

The detailed description to follow includes references to the drawings listed below, in which like reference numerals identify like elements unless otherwise indicated. The drawings depict non-limiting examples of features of the disclosed subject matter and are not exhaustive of all possible examples or features. Those of ordinary skill in applicable technology fields will recognize that the disclosed subject matter encompasses, in addition to the examples illustrated in the drawings, embodiments with structurally or functionally equivalent features.

DETAILED DESCRIPTION

Figure 1:
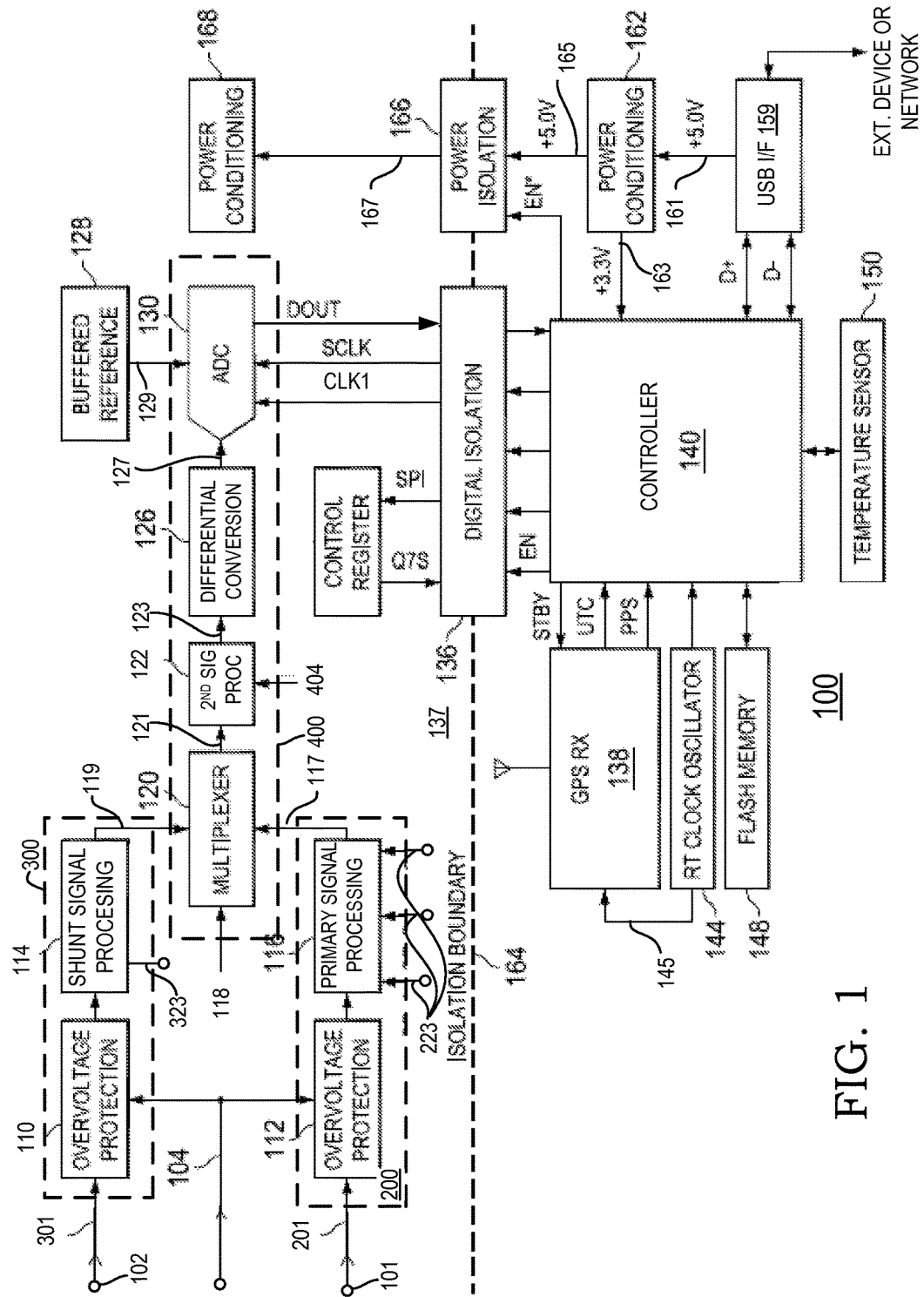
FIG. 1 is a block diagram of a digital multimeter.

Digital multimeters disclosed herein may exhibit a very high and very stable input impedance across all available ranges by employing an input stage featuring a multi mega-ohm input resistor configured to convey a received signal to an internal node, referred to herein as a summing node, and a variable gain, variable bandwidth input buffer connected to the summing node. The input buffer may function as the first stage of the digital multimeter and may be configured as a negative feedback operational amplifier circuit coupled between the summing node and a first stage output node. The input buffer may include multiple, individually selectable, feedback paths each of which, whenever selected, is connected between the output of the input buffer and the summing node. The input buffer may include, in addition to the selectable feedback paths, a non-selectable feedback path, referred to herein as a fixed feedback, that is permanently connected between the input buffer output and the summing node.

Each of the feedback paths, whether fixed or selectable, may have a corresponding impedance and a corresponding gain-bandwidth characteristic. The fixed feedback path, when included, provides a baseline gain-bandwidth configuration and a particular gain-bandwidth configuration may be achieved by appropriate selection of the selectable feedback paths. In at least one embodiment, the input buffer supports four or more gain-bandwidth configurations including high-gain, wideband; high-gain, low-pass; low-gain, wideband, and low-gain, low-pass configurations.

The multi mega-ohm input resistor may have a resistance equaling or exceeding 100 MΩ to reduce measurement error sensitivity to higher resistivity soils typically found in certain applications and environments including cathodic protection environments in which the resistivity of the soil is inherently a component of the measurement circuit. The input resistor may be implemented as a plurality of input resistors connected in series. In at least one embodiment, for example, the input resistor comprises a set of ten 10 MΩ resistors, but other embodiments may use fewer or more input resistors and may use input resistors of lower or higher resistance, or an input resistor string that includes individual resistors with resistances that differ from one another in nominal value.

Disclosed multimeters may accommodate the ultra-high input impedance by aggressively limiting leakage currents, biasing currents, and offset voltages. The input buffer feedback paths may include a switch that, whenever closed, connects the feedback path, including the feedback path's impedance elements, to the summing node. To ensure zero or substantially zero leakage current at the summing node, some embodiments may include a compound and specially configured switch, referred to herein as an L-switch or a zero voltage switch, that maintains 0 V on both switch terminals independent of whether the switch is open or close.

The input buffer may include an AC-rejecting configuration for filtering a small amplitude DC component of a particular primary signal that includes a large amplitude AC component. The inclusion of A/C-rejecting pole in the buffer stage may beneficially enable the digital multimeter to measure a sub-volt DC signal that is electrically hidden within in a large magnitude AC signal, without imposing undesirably high rail-to-rail voltage swings on the active circuitry.

By combining an ultra-high input impedance and aggressive first stage noise attenuation in a meter that offers multiple magnitudes of DC gain, any one of which may be configured in a low-pass or wide-pass filtering configuration, disclosed meters obtain precise measurements of small DC signals in cathodic protection and other environments experiencing random and induced noise of an amplitude exceeding the amplitude of a DC signal-of-interest by orders of magnitude.

Disclosed multimeters include battery-powered meters suitable for use in remote field locations that may lack a readily accessible source of useable electric power. Battery powered embodiments of disclosed multimeters may draw extremely low operating current, e.g., 0.1 mA or less, to achieve an acceptable battery life. Some battery-powered embodiments of disclosed multimeters may adhere to constraints on the maximum rail-to-rail voltage swings to which operational amplifiers and other elements of the multimeter are subjected. As one non-limiting example, a battery powered embodiment of the digital multimeter may employ a 9 V battery and may specify a maximum permitted rail-to-rail voltage swing of approximately 9 V or less. Other embodiments may use different battery voltages, different maximum voltage swing restrictions, or both. While constraining the acceptable rail-to-rail swings may beneficially reduce the amount of voltage conversion and voltage regulation required, doing so may necessitate early and aggressive attenuation and filtering of noise components in the received signal.

Throughout this disclosure, a hyphenated form of a reference numeral refers to a specific instance of an element and an un-hyphenated form of the reference numeral refers to the element generically or collectively. Thus, for example, widget 12-1 refers to a particular instance of a widget, which may be referred to collectively as widgets 12 and any one of which may be referred to generically as a widget 12.

Referring now to the drawings, FIG. 1 illustrates elements of a digital multimeter 100 including various features disclosed herein. The digital multimeter 100 illustrated in FIG. 1 includes a first input node referred to herein as primary input node 101 for receiving signals referred to herein as primary signals 201 and a second input node, referred to herein as shunt input node 102, for receiving signals referred to herein as shunt signals 301. The digital multimeter 100 illustrated in FIG. 1 includes some components, circuits, or stages that are dedicated either to primary signals 201 or to shunt signals 301. The illustrated digital multimeter 100 also includes some components, circuits, or stages that are shared, i.e., applied to primary signals 201 as well as shunt signals 301. Thus, for example, FIG. 1 illustrates multiple signal processing stages of digital multimeter 100 including a primary input stage 200 and a shunt input stage 300, which are dedicated stages, and a second stage 400, which is a shared stage. The dedicated stages may enable digital multimeter 100 to provide a wide range of gain-bandwidth characteristics while the shared stage(s) may beneficially contribute to reduced size, complexity, power consumption, and cost.

Figure 2:
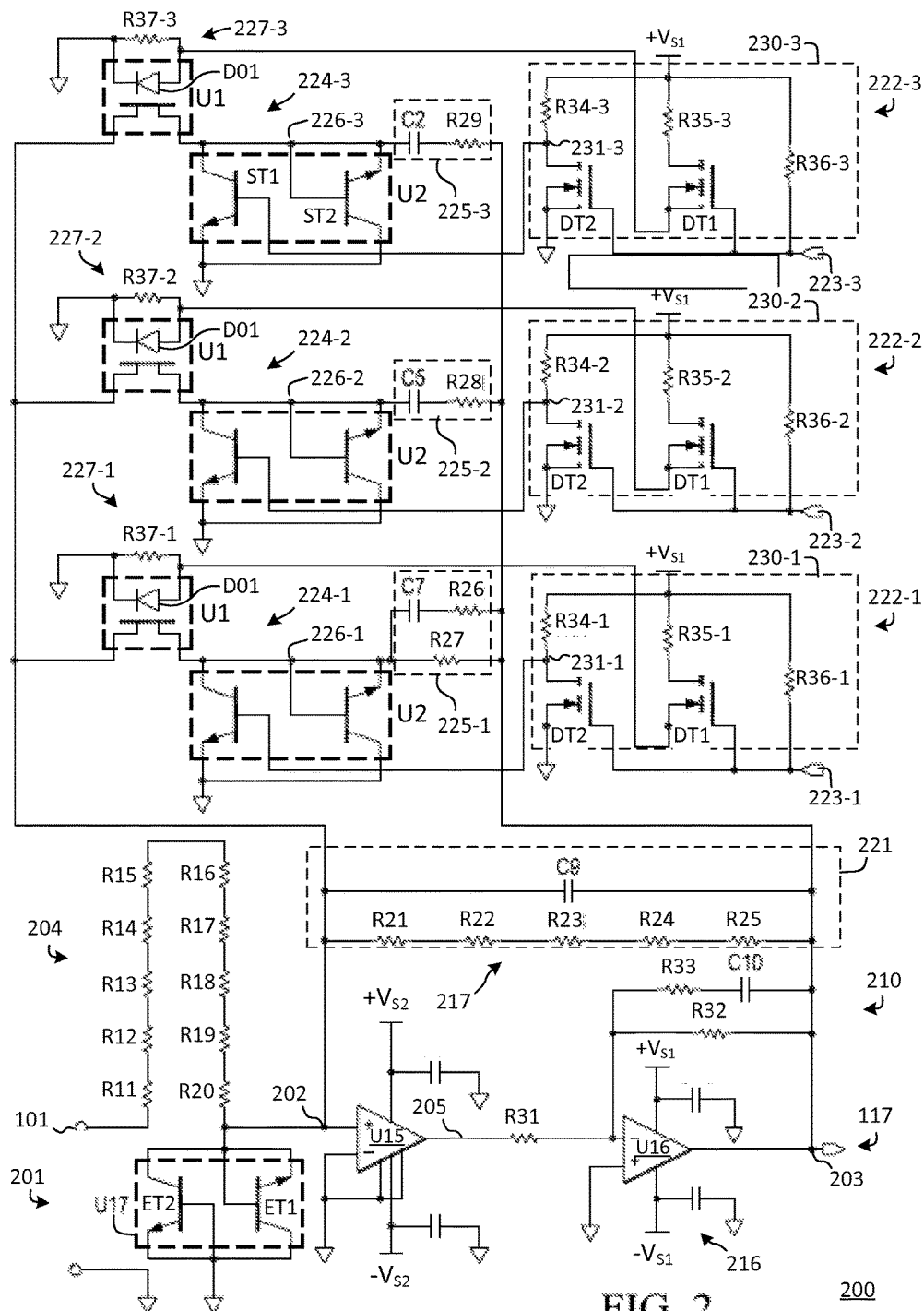
FIG. 2 illustrates an input stage of a primary side of the digital multimeter.
Figure 3:
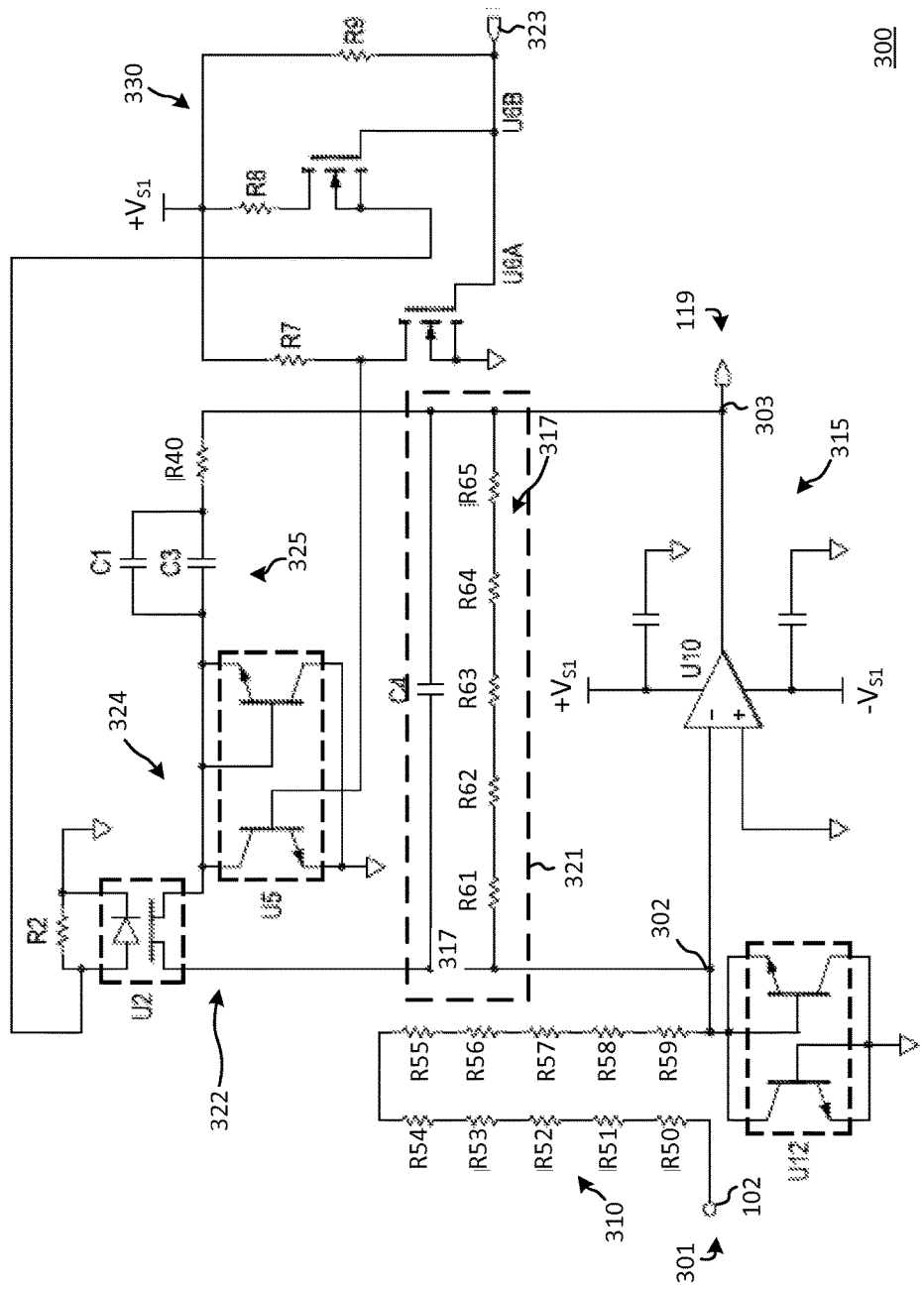
FIG. 3 illustrates an input stage of a shunt side of the digital multimeter.
Figure 4:
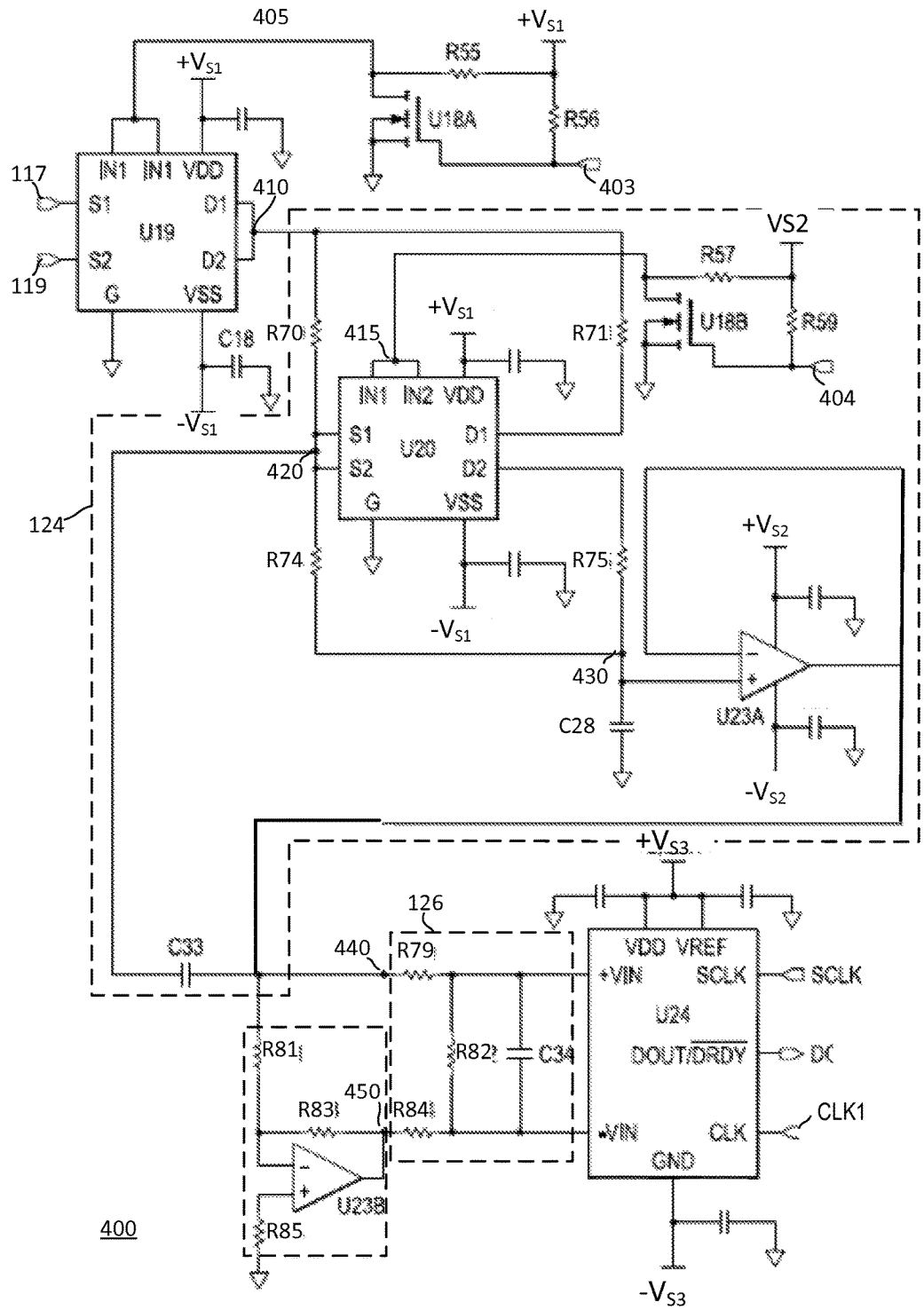
FIG. 4 illustrates a second stage of the digital multimeter.

The primary input stage 200, described in more detail with respect to FIG. 2, may attenuate, filter, buffer, or perform other conditioning of primary signal 201 to produce an intermediate primary signal 117 that is provided to second stage 400, described in more detail with respect to FIG. 4. Similarly, shunt input stage 300, described in more detail with respect to FIG. 3, may attenuate, filter, buffer, or perform other conditioning of shunt signal 301 to produce an intermediate shunt signal 119 that is provided to second stage 400. The second stage 400 illustrated in FIG. 1 is a shared resource that operates either on intermediate primary signal 117 or intermediate shunt signal 119 in accordance with a shunt/voltage selection input 118.

The primary input stage 200 illustrated in FIG. 1 includes primary overvoltage protection circuit 112 and a primary signal processing circuit 116. Similarly, shunt input stage 300 includes shunt overvoltage protection circuit 110 and a shunt signal processing circuit 114. Primary overvoltage protection circuit 112 and primary signal processing circuit 116 may be integrated into a single circuit board or component. Similarly, shunt overvoltage protection 110 and shunt signal processing circuit 114 may be integrated into a single circuit board or component.

The primary signal processing circuit 116 illustrated in FIG. 1 receives three primary configuration signals 223, which may select or determine the gain-bandwidth configuration of primary signal processing circuit 116. The shunt signal processing circuit 114 illustrated in FIG. 1 receives a single shunt configuration signal 323, which may select or determine the gain-bandwidth configuration of shunt signal processing circuit 114. Although FIG. 1 illustrates primary signal processing circuit 116 receiving multiple configuration inputs and shunt signal processing circuit 114 receiving a single configuration input, other embodiments may provide more or fewer configuration inputs to either signal processing circuit.

In at least one embodiment, the maximum DC gain of primary signal processing circuit 116 differs from the maximum DC gain of the shunt signal processing circuit 114 by at least an order of magnitude. In embodiments suitable for applications in which the amplitude of the signal noise may exceed the amplitude of the signal-of-interest by one or more orders of magnitude, a magnitude of the maximum configurable DC gain of primary signal processing circuit 116 may be less than 1. In at least some of these embodiments, however, the magnitude of the maximum DC gain of shunt signal processing circuit 114 may be greater than 1.

The second stage 400 illustrated in FIG. 1 includes a multiplexer 120, which receives shunt selection input 118 as a control input that passes either the intermediate primary signal 117 or the intermediate shunt signal 119 as the selected signal 121 to a second signal processing circuit 122. The second signal processing circuit 122 illustrated in FIG. 1 performs additional processing of the selected signal 121 and outputs a processed signal 123 to a differential conversion circuit 126. Differential conversion circuit 126 converts the processed signal 123 received from second signal processing circuit 122 to a differential signal, performs additional filtering, and outputs differential signal 127 to an analog-to-digital converter (ADC) 130. In at least one embodiment, the frequency response of second signal processing circuit 122 is configurable in any of at least two configurations according to an AC/DC selection input 404.

The ADC 130 illustrated in FIG. 1 receives one or more highly stable and precise supply voltage(s) 129 from a buffered reference circuit 128. The ADC 130 may employ an nth-order delta sigma modulator (not depicted explicitly) and generates a digital and serialized data output DOUT in accordance with differential signal 127. The ADC 130 illustrated in FIG. 1 receives a first clock signal CLK1 to drive the converter's modulator and an independent serial clock signal SCLK to drive the converter's serial interface. In other embodiments, ADC 130 may employ a single clock signal, shared by the modulator and the serial interface.

The DOUT signal illustrated in FIG. 1 is provided, via a digital isolation circuit 136, to a controller 140. More generally, the digital multimeter's signal measurement components "north" of isolation boundary 164 are galvanically isolated from the digital multimeter components "south" of isolation boundary 164 by digital isolation circuit 136 and power isolation circuit 166, either of which may include optical, capacitive, or inductive isolation components or a combination thereof.

The digital multimeter 100 illustrated in FIG. 1 further includes a flash memory 148, a power conditioning circuit 162, a global position system (GPS) receiver 138, a real time clock oscillator 144, and a temperature sensor 150. Digital multimeter 100 may be configured to communicate with an external device or network via a universal serial bus (USB) interface 159. GPS receiver 138, may be used to provide a source of timestamp information for controller 140.

The USB interface 159 illustrated in FIG. 1 routes a 5.0 V supply voltage signal 161 to power conditioning circuit 162 and provides a differential data signal D+/D- to controller 140. The power conditioning circuit 162 illustrated in FIG. 1 receives the 5.0 V supply signal from USB interface 159, provides a 3.3 V supply voltage 163 to controller 140, and a provides a 5.0 V supply signal 165 to power isolation circuit 166, which provides isolated power signal 167 to the power conditioning circuit 168.

Referring now to FIG. 2, primary input stage 200 is shown in greater detail. In the descriptions that follow, references to "low frequency" may refer to frequencies less than or equal to approximately 60 Hz. In at least one embodiment, primary input stage 200 provides preliminary attenuation and filtering of a primary signal 201, i.e., a signal received at primary input node 101 to produce intermediate primary signal 117 at a primary input stage output node 203. Primary input stage 200 may be modeled as an ideal or nearly ideal negative feedback operational amplifier circuit that receives an input voltage Vin and produces an output voltage Vout, where Vout/Vin equals Zf/Zin, Zin refers to an input impedance between primary input node 101 and an internal node referred to herein as a primary summing node 202, and Zf refers to the impedance between primary summing node 202 and primary input stage output node 203.

The input impedance Zin of the primary input stage 200 illustrated in FIG. 2 is dominated by input resistor 204, which is shown as a 100 MΩ resistor and may be referred to herein as multi mega-ohm input resistor 204. The multi mega-ohm input resistor 204 is illustrated in FIG. 2 as a ten series-connected 10 MΩ resistors R11 through R20 coupled between primary input node 101 and primary summing node 202. In this embodiment, the use of multiple, smaller resistors may beneficially reduce the voltage coefficient of input resistor 204 any may enable the use of components that are more readily available, more reliable or precise, or both. In addition, the power dissipated in ten 10 MΩ resistors connected in series is 1/10 the power dissipated in a signal 100 MΩ resistor for the same current, potentially resulting in less thermally induced impedance drift and less overall power consumption. Moreover, the use of multiple smaller resistors provides an additional measure of overvoltage protection by effectively distributing any over voltage spike across 10 elements. The feedback impedance Zf is determined by one or more feedback paths that may be connected in parallel with one another between primary summing node 202 and primary input stage output node 203.

The depicted primary input stage 200 includes two operational amplifiers, U15 and U16, coupled in series between summing node 202 and primary input stage output node 203. The first operational amplifier U15 includes a non-inverting input coupled to receive the signal at primary summing node 202 and an output configured to output a signal 205 to the inverting input of second operational amplifier U16 via resistor R31. In some embodiments, first operational amplifier U15 is a low-bias operational amplifier characterized by an extremely low input bias requirement, e.g., a femtoampere biasing current and an extremely low offset voltage, e.g., single digit microvolt offset or below. The output of second operational amplifier U16 is shown being fed back to its inverting input via a feedback path 210. In the embodiment depicted in FIG. 2, feedback path 210 includes an upper branch, comprising a resistor R33 in series with a capacitor C10, in parallel with a lower branch that includes a resistor R32. In at least one embodiment that employs "standard value" components, i.e., components that are readily obtainable from one or more commercial providers or distributors, a representative value of resistor R33 is 1 KΩ, a representative value of capacitor C10 is approximately 220 pF, a representative value of resistor R32 is approximately 40.2 KΩ, and a representative value of the U16 input resistor, R31, is approximately 10 KΩ. FIG. 2 illustrates U16 powered by supply voltages +VS1 and -VS1 and U15 power by supply voltages +VS2 and -VS2. In at least one embodiment, +VS1 may indicate an +8.0 V supply voltage and +VS2 may indicate a +2.75 V supply voltage. Other embodiments may use different values of supply voltages for VS1, VS2, or both.

Assuming the open circuit gains of U15 and U16 are reasonable, e.g., greater than 1000, the gain, G, of primary input stage 200 is given simply by:

$$G = \frac{Vout}{Vin} = \frac{Zf}{Zin} = \frac{Zf}{Rin}$$

The primary input stage 200 depicted in FIG. 2 includes multiple individually selectable impedance paths 222 and a fixed-presence feedback path 221 that support feedback path configurations with various gain-bandwidth characteristics including low-gain and high-gain configurations and wide-band or AC filtering and low-pass or DC filtering configurations selectable via primary configuration inputs 223-1 through 223-3. Primary input stage 200 outputs intermediate primary signal 117 at primary input stage output node 203, which is coupled to the second stage 400, described below with respect to FIG. 4.

Qualitatively, primary input stage 200 performs preliminary signal attenuation sufficient to accommodate signals containing, in addition to a signal-of-interest with a comparatively small DC magnitude, signal noise with comparatively large peak-to-peak variations. In one non-limiting and exemplary application, the signal-of-interest is a DC signal with an amplitude in the range between −1.5 and 1.5 V while the noise component, which may include an induced AC component associated with a nearby high power transmission line, may have a peak-to-peak amplitude approaching or exceeding 200 VAC. In addition to providing preliminary attenuation, primary input stage 200 may also perform at least some filtering of the input signal. In some embodiments, primary input stage 200 functions as the first pole of a multi-pole filter.

The embodiment of primary input stage 200 illustrated in FIG. 2 is configurable in any of eight feedback path impedances to implement any of eight gain-bandwidth profiles including, as non-limiting examples described in greater detail below, a high-gain, wide-pass configuration, a low-gain, low-pass configuration, a high-gain, low-pass configuration, and a low-gain, low-pass configuration. For applications in which significant attenuation of noise components may be required, the high-gain configurations, despite their names, may have a gain of less than unity, i.e., may attenuate the signal.

The fixed-presence feedback path 221 depicted in FIG. 2 provides a default value of Zf and a default gain-bandwidth configuration of primary input stage 200. Zero or more of the three individually selectable feedback paths 222-1 through 222-3, may be coupled in parallel with fixed-presence feedback path 221 to achieve as many as eight gain-bandwidth configurations. Although FIG. 2 depicts primary input stage 200 with a fixed-presence feedback path 221 and three switchable feedback paths 222 configurable to implement eight gain-bandwidth configurations, other embodiments may omit a fixed-presence feedback path, employ more or fewer selectable feedback paths, and support a different number of available gain-bandwidth configurations.

When none of the selectable feedback paths 222 are selected, i.e., none of the selectable feedback paths 222 are coupled in parallel with fixed-presence feedback path 221, fixed-presence feedback path 221 provides a high-gain wideband (HW) configuration of primary input stage 200. The HW configuration may be characterized as providing modest and uniform attenuation with substantially no distortion or filtering within the frequency band of interest, which may refer to frequencies less than 1 kHz in some embodiments, frequencies less than 100 Hz in some embodiments, or frequencies less than or equal to approximately 60 Hz in still other embodiments. The HW configuration of primary input stage 200 may have a DC gain of approximately −6 dB, i.e., a DC gain of 0.5, a −6 dB drop in gain at a frequency of approximately 1 kHz, and a gain roll off of approximately −20 dB/decade at higher frequencies. The fixed-presence feedback path 221 illustrated in FIG. 2 includes a small capacitor C9 in parallel with a very large resistor 217. In at least one standard value embodiment, a representative value of capacitor C9 is approximately 2.7 pF and a representative value of resistor 217 is approximately 50 MΩ. As illustrated in FIG. 2, resistor 217 is implemented with a set of five series-connected 10 MΩ resistors R21 through R25, but other embodiments may use a different number of resistors, including one resistor, for resistor 217.

Although the selectable feedback paths 222 may be connected in parallel with fixed-presence feedback path 221 in as many as seven configurations, in addition to the HW configuration just described, in which none of the selectable feedback paths 222 is connected, the following description illustrates three particular configurations that, together with the HW configuration, provide a voltage measurement stage configurable in any of four gain-bandwidth profiles. Other embodiments may include more, fewer, or different configurations that emphasize different combinations of gain-bandwidth characteristics. As one non-limiting example, whereas the four primary input stage configurations described herein all perform some degree of signal attenuation, i.e., gain <1, other embodiments of primary input stage 200 may include a configuration that employs amplifying gain, i.e., gain >1 for DC or at least some portion of the frequency spectrum.

The primary input stage 200 illustrated in FIG. 2 includes a low-gain, widepass (LW) feedback path 222-1 that, when connected in parallel with the fixed-presence feedback path 221, with feedback paths 222-2 and 222-3 disconnected, produces an LW configuration of primary input stage 200. The LW configuration may be characterized as exhibiting aggressive DC and low frequency attenuation in combination with sharp gain roll off at frequencies above approximately 1000 Hz. The LW configuration of primary input stage 200 may have a DC gain of approximately −40 dB, i.e., a DC gain of approximately 0.01, a −6 dB drop in gain at a frequency of approximately 1000 Hz, and a gain roll off of approximately −20 dB/decade at higher frequencies. The impedance element 225-1 of the LW feedback path 222-1 illustrated in FIG. 2 includes a capacitor C7 in series with a resistor R26, both of which are in parallel with a resistor R27. In at least one standard value embodiment, a representative value of capacitor C7 is approximately 220 pF, a representative value of resistor R26 is 499Ω, and representative value of resistor R27 is approximately 1 MΩ.

The primary input stage 200 of FIG. 2 further includes a high-gain, low-pass (HL) feedback path 222-2 that, when connected in parallel with the fixed-presence feedback path 221, with feedback paths 222-1 and 222-3 disconnected, produces an HL configuration of primary input stage 200. The HL configuration may be characterized as exhibiting modest DC attenuation in combination with sharp gain roll off at frequencies above approximately 10 Hz. The HL configuration of primary input stage 200 may have a DC gain of approximately −6 dB, i.e., a gain of approximately 0.5, a −6 dB drop in gain at a frequency of approximately 10 Hz and gain roll off of approximately −20 dB/decade at higher frequencies. An impedance element 225-2 of the HL feedback path 222-2 illustrated in FIG. 2 may include a capacitor C5 in series with resistor R28. In at least one standard value embodiment, a representative value of capacitor C5 is approximately 430 pF and a representative value of resistor R28 is approximately 499Ω.

The primary input stage 200 of FIG. 2 further includes a low-gain, low-pass (LL) feedback path 222-3 that, when connected in parallel with the fixed-presence feedback path 221 and LL feedback path 222-1, with feedback path 222-2 disconnected, produces an LL configuration of primary input stage 200. The LL configuration may be characterized as exhibiting DC attenuation in combination with sharp gain roll off at frequencies above approximately 10 Hz. The LL configuration of primary input stage 200 may have a DC gain of −40 dB, a −6 dB drop in gain at a frequency of approximately 10 Hz, and frequency roll off of approximately −20 dB/decade at higher frequencies. An impedance element 225-3 of the LL feedback path 222-3 illustrated in FIG. 2 may include a capacitor C2 in series with a resistor R29. In at least one standard value embodiment, a representative value of capacitor C2 is approximately 0.022 uF and a representative value of resistor R29 is approximately 499Ω.

Table 1 below summarizes the four gain-bandwidth configurations of primary input stage 200, indicating representative gains (dB), bandwidths and which of the selectable feedback paths 222 are active for each of the four configurations. Other embodiments of primary input stage 200 may exhibit different gain and bandwidth values.

TABLE 1

| GAIN STATE | BANDWIDTH STATE | FB PATH 221 | FB PATH 222-1 | FB PATH 222-2 | FB PATH 222-3 | DC GAIN (dB) | BANDWIDTH (Hz) |
|---|---|---|---|---|---|---|---|
| HIGH | WIDEBAND | FIXED | OFF | OFF | OFF | −6 | 1000 |
|  | LOW PASS | FIXED | OFF | ON | OFF | −6 | 10 |
| LOW | WIDEBAND | FIXED | ON | OFF | OFF | −40 | 1000 |
|  | LOW PASS | FIXED | ON | OFF | ON | −40 | 10 |

FIG. 2 illustrates a driver circuit 230 corresponding to each selectable feedback path 222 and controlled by a corresponding primary input stage configuration input 223. Each driver circuit 230 illustrated in FIG. 2 controls a switch circuit referred to herein as an L-switch 224, which provides two orthogonal current paths to a node referred to herein as impedance node 226, which is connected to one of the two terminals of an optical switch U1. In the configuration illustrated in FIG. 2, in which impedance node 226 is always coupled to ground as described below, each L-switch 224 is alternatively referred to herein as a zero volt switch.

Each driver circuit 230 illustrated in FIG. 2 includes a first driver transistor DT1 and a second driver transistor DT2, both of which are controlled by a primary input stage configuration input 223. When a primary input stage configuration input 223 is driven high, second driver transistor DT2 turns on and diverts current flowing through resistor R34 from activating first switching transistor ST1, thereby turning first switching transistor ST1 off. At the same time, with configuration input 223 driven high, first driver transistor DT1 functions as a current source and the IDS current of driver transistor DT1 flows directly into LED circuit 227, thereby activating optical switch U1 and connecting impedance node 226 to primary summing node 202. Because summing node 202 is virtually grounded through operational amplifier U15, impedance node 226 is virtually grounded when optical transistor U1 is on. In this state, with optical switch U1 closed and second switch U2 open, any current flowing through the applicable impedance element 225 flows directly through optical switch U1 to primary summing node 202.

When a primary input stage configuration input 223 is asserted low, first driver transistor DT1 turns off and optical switch U1 opens as current into LED circuit 227 is cut off. At the same time, asserting configuration input 223 low turns second driver transistor DT2 off, forcing current flowing through resistor R34 into the base terminal of shunting transistor ST1, thereby turning shunting transistor ST1 on and clamping impedance node 226 to ground. Accordingly, whether shunted to electrical ground by shunting transistor ST1 when optical switch U1 is off or virtually coupled to ground through optical switch U1 and operational amplifier U15 when optical switch U1 is on, impedance node 226 remains at 0 V. Since each optical switch U1 includes a terminal connected to summing node 202, the voltage of both optical switch terminals is maintained at 0 V and the voltage across each optical switch U1 is also maintained at 0 V, independent of the on/off state of optical switch U1.

The second shunting transistor ST2, configured with its base and emitter terminals shorted, effectively functions as a diode that limit impedance node 226 from transitioning or spiking negative beyond the small voltage required to forward bias the pn junction at the base-collector interface and this condition is maintained regardless of whether optical switch U1 is closed.

The impedance element 225 of each selectable feedback path 222 illustrated in FIG. 2 is connected between a corresponding impedance node 226 and primary input stage output node 203. Each selectable feedback path 222 illustrated in FIG. 2 also includes a switching circuit referred to herein as L-switch 224 configured to connect the corresponding impedance node 226 either to ground or to the primary summing node 202 in accordance with the corresponding primary input stage configuration input 223. Each L-switch 224 depicted in FIG. 2 includes an optical switch U1 configured to connect, when closed, impedance node 226 to primary summing node 202. The first switches U1 illustrated in FIG. 2 are optically activated switches. Each depicted L switch 224 also includes a second switch U2 configured, when closed, to shunt impedance node 226 to ground. Each primary input stage configuration input 223 controls its corresponding L-switch 224 with a driver circuit 230. In at least one embodiment, driver circuit 230 operates to ensure that (a) one of the two switches U1 and U2 is always closed and (b) the two switches U1 and U2 are never both closed at the same time. Thus, each L-switch 224 depicted in FIG. 2 functions as a "zero volt switch" that maintains 0 V across the output terminals of each U1 switch independent of whether the applicable first stage configuration input 223 is asserted. Maintaining 0 V across each U1 switch beneficially enables implementations exhibiting zero or substantially zero leakage current flowing into primary summing node 202 from the various feedback paths 222.

The primary input stage 200 illustrated in FIG. 2 includes an electrostatic discharge (ESD) circuit U17 coupled to primary summing node 202 to provide overvoltage protection. The ESD circuit U17 illustrated in FIG. 2 includes a pair of NPN bipolar junction transistors, identified as first ESD transistor ET1 and second ESD transistor ET2. The base and emitter terminals of first ESD transistor ET1 are shorted and connected to primary summing node 202 while the collector terminal of ET1 is grounded. In this arrangement, first ESD transistor ET1 functions as a diode with its anode connected to primary summing node 202. Conversely, the base and emitter terminals of second ESD transistor ET2 are shorted and grounded while the collector terminal is connected to primary summing node 202, thereby functioning as a diode with its anode connected to ground. Thus, ET1 and ET2 function as an antiparallel diode pair to rapidly dissipate any charge accumulating at summing node 202.

The digital multimeter 100 illustrated in FIG. 1 includes a shunt input stage 300 configured to receive a shunt signal 301 at shunt input node 102 and perform preliminary attenuation and filtering to produce intermediate shunt signal 119, which is provided to multiplexor 120 of second stage 400. In at least one embodiment, shunt input stage 300 provides one or more gain-bandwidth profiles that differ from the gain-bandwidth profiles available via primary input stage 200, including one or more profiles having a different DC gain than the profiles supported by primary input stage 200. Shunt input stage 300 may include or support more or fewer selectable gain-bandwidth configurations than primary input stage 200.

In at least one embodiment, shunt input stage 300 includes a negative feedback operational amplifier circuit that, like primary input stage 200, includes a fixed-presence feedback path in parallel with one or more selectable feedback paths to achieve two or more obtainable gain-bandwidth configurations. In at least one embodiment in which the maximum achievable gain for primary input stage 200 is an attenuating gain, i.e., a gain <1, one or more configurations of shunt input stage 300 may provide an amplifying gain for DC or at least some portion of the frequency spectrum. In at least one embodiment, one or more configurations of shunt input stage 300 provide a gain of 5 or more for DC and at least some portion of the frequency spectrum.

Referring now to FIG. 3, a shunt input stage 300 is illustrated. The shunt input stage 300 depicted in FIG. 3 includes shunt input stage input node 102 receiving shunt signal 301 Shunt input stage 300 may provide gain-bandwidth configurations in addition to those provided by primary input stage 200. In at least one embodiment, shunt input stage 300 offers a maximum DC gain that is an order of magnitude or more higher than the maximum DC gain of primary input stage 200.

The shunt input stage 300 illustrated in FIG. 3 includes a shunt input resistor 310 connected between shunt input node 102 and a shunt summing node 302. The shunt input resistor 310 illustrated in FIG. 3 is a 100 KΩ resistor comprised of ten series-connected individual 10 KΩ resistors, R50 through R59. Other embodiments of shunt input resistor 310 may include more or fewer individual resistors and may include individual resistors of different values.

The shunt input stage 300 of FIG. 3 includes a negative feedback operational amplifier circuit 315 that includes a fixed-presence feedback path 321 and a single selectable feedback path 322. The selectable feedback path 322 illustrated in FIG. 3 receives a shunt configuration signal 323 and includes a driver circuit 330, both of which are functionally analogous to the primary input stage configuration inputs 223 and driver circuit 230 of FIG. 2. The shunt input stage 300 illustrated in FIG. 3 includes an impedance element 325 and an L-switch circuit 324 that functions in a manner analogous to the L-switches 224 of FIG. 2. The L-switch 324 of FIG. 3 is configured to connect impedance element 325, in parallel with fixed-presence feedback path 321, between the shunt summing node 302 and the shunt input stage output node 303.

The fixed-presence feedback path 321 of FIG. 3 provides a default gain-bandwidth configuration that may be modified by selecting the selectable feedback path 321 to achieve a second gain-bandwidth configuration. Although FIG. 3 depicts shunt input stage 300 with a fixed-presence feedback path 321 and one selectable feedback path 322 to configure the shunt input stage in either of two gain-bandwidth configurations, other embodiments may omit a fixed-presence feedback path, employ more or fewer selectable feedback paths, and support a different number of available gain-bandwidth configurations.

When the selectable feedback path 322 is not selected, the fixed-presence feedback path 321 illustrated in FIG. 3 provides an amplifying gain, wideband (AW) configuration of shunt input stage 300. The AW configuration of shunt input stage 300 may be characterized as providing modest and uniform amplifying gain for DC and all frequency components of interest with little or no distortion. The AW configuration of shunt input stage 300 may have a DC gain of approximately 14 dB, i.e., a gain of approximately 5, a −6 dB drop in gain at a frequency of approximately 1 kHz, and a gain roll off of approximately −20 dB/decade at higher frequencies. The fixed-presence feedback path 321 illustrated in FIG. 3 includes a capacitor C4 in parallel with a resistor 317. In at least one embodiment, the capacitor C4 is a 270 pF capacitor and the resistor 317 is a 500 KΩ resistor.

The shunt input stage 300 of FIG. 3 includes an amplifying gain, low-pass (AL) feedback path 322, which when connected in parallel with the fixed-presence feedback path 321, produces an AL configuration of shunt input stage 300. The AL configuration of shunt input stage 300 may be characterized as providing modest amplifying gain at DC and low frequencies with fairly sharp gain roll off at higher frequencies. The AL configuration of shunt input stage 300 illustrated in FIG. 3 may have a DC gain of approximately 14 dB, i.e., a gain of approximately 5, a −6 dB drop in gain at a frequency of approximately 10 Hz, and a gain roll off in the range of approximately −20 dB/decade at higher frequencies. The impedance element 325 of AL feedback path 322 illustrated in FIG. 3 includes a resistor R40 in series with a pair of parallel-coupled capacitors C1 and C3. In at least standard value embodiment, a representative value of resistor R40 is approximately 499Ω and a representative value for each of the capacitors C1 and C3 is approximately 22 nF. Although FIG. 3 illustrates impedance element 325 with two distinct, equal value capacitors C1 and C3, other embodiments may use two or more capacitors of different values or a single capacitor of value C1+C3.

Table 2 below summarizes the gain-bandwidth configurations of shunt input stage 300. Other embodiments of the shunt input stage may have other gain values.

TABLE 2

SHUNT FIRST STAGE GAIN AND BANDWIDTH

| GAIN STATE | BAND- WIDTH STATE | FB PATH 321 | FB PATH 322 | DC GAIN (dB) | BAND- WIDTH (Hz) |
|---|---|---|---|---|---|
| High (Amplifying) | High | FIXED | OFF | +14 | 1000 |
|  | Low | FIXED | ON | +14 | 10 |

Referring now to FIG. 4, a second stage 400 of digital multimeter 100 is illustrated. The second stage 400 illustrated in FIG. 4 processes either the intermediate primary signal 117 received from primary input stage 200 or the intermediate shunt signal 119 received from shunt input stage 300. A primary/shunt selection input 403 determines whether intermediate primary signal 117 or intermediate shunt signal 119 is passed through an analog switch U19 to a node 410. The node 410 illustrated in FIG. 4 provides an input to a second filter stage 124, which performs additional processing of signals received from node 410 and produces a filtered signal at filtered signal node 440.

The second stage 400 illustrated in FIG. 4 receives two control inputs, a primary/shunt selection input 403, and a AC/DC selection input 404. Primary shunt/switch selection input 403 determines whether intermediate shunt signal 119 from shunt input stage 300 of FIG. 3 or intermediate primary signal 117 from primary input stage 200 of FIG. 2 is forwarded to node 410 and, from there, to second filter stage 124. In at least one embodiment, primary/shunt selection input 403 drives the transistor switch U18A that provides a control input 405 to a 2-port analog switch U19. The analog switch U19 illustrated in FIG. 2 includes a pair of oppositely-triggered, single-pole single-throw switches connecting first and second inputs S1 and S2 to first and second output terminals D1 and D2 respectively. The transistor switch U18A illustrated in FIG. 4 drives control inputs IN1 and IN2 of analog switch U19 with a common signal. In the illustrated configuration, analog switch U19, depending upon the voltage at node 415 provides to control inputs IN1 and IN2, will either connect first input S1 to first output D1 or second input S2 to second output D2, but not both.

The first input S1 of analog switch U19 depicted in FIG. 4 receives intermediate primary signal 117 from primary input stage 200 (FIG. 2) and the second input S2 of analog switch U19 receives intermediate shunt signal 119 from shunt input stage 300 (FIG. 3). First output D1 and second output D2 of analog switch U19 are shorted together in the second stage 400 illustrated in FIG. 4 to form node 410. Depending upon primary/shunt selection input 403, control input 405 will connect either intermediate primary signal 117 or intermediate shunt signal 119 to node 410.

FIG. 4 illustrates a first pair of resistors R70 and R71 both connected to a common node, node 410. Resistor R70 is connected between node 410 and an S1 pin of second analog switch U20 while resistor R71 is connected between node 410 and a D1 pin of second analog switch U20. Similarly, a second pair of resistors R74 and R75 are connected to a common node, node 430. Resistor R74 is connected between node 430 and an S2 pin of second analog switch U20 while resistor R75 is connected between node 430 and a D2 pin of second analog switch U20. FIG. 4 further illustrates the S1 and S2 pins of second analog switch U20 both connected to a common node, node 420.

The illustrated configuration of second filter stage 124 employs second analog switch U20 to switch between high impedance and low impedance configurations of second filter stage 124, with a corresponding changing in the location of the filter stage's frequency pole. When second analog switch U20 is activated by an appropriate voltage on control input pins IN1 and IN2, resistor R71 is connected in parallel with resistor R70 while resistor R75 is connected in parallel with resistor R74 to lower the impedance and thereby alter the transfer function of second filter stage 420.

The AC/DC selection input 404 selects between a wideband (AC) filtering configuration and a low-pass (DC) filtering configuration of second stage 400. The AC/DC selection input drives a transistor U18B that determines the voltage of control inputs IN1 and IN2 via node 415. Unlike the IN1 and IN2 inputs of first analog switch U19, the IN1 and IN2 inputs of second analog switch U20 have the same polarity. Whenever AC/DC selection input 404 is asserted low, second analog switch U20 is activated, thereby coupling resistor R71 in parallel with resistor R70 between node 410 and node 420 and further connecting resistor R75 in parallel with resistor R74 between node 420 and node 430. In at least one standard value embodiment, a representative value of resistors R70 and R74 is approximately 113 KΩ and a representative value of resistors R71 and R75 is approximately 1.13 KΩ. In this configuration, whenever second analog switch U20 is on, the substantially lower resistances of R71 and R75 effectively replace the corresponding resistors R70 and R74.

A capacitor C33 is illustrated in FIG. 4 connected between node 420 and filtered signal node 440. The voltage at node 430 is mirrored at filtered signal node 440 by an operational amplifier U23A, which is illustrated with its output terminal directly connected to its inverting input terminal. A capacitor C28 is connected between ground and intermediate node 430, which is connected to the non-inverting input of operational amplifier U23A. Capacitors C28 and C33 may be implemented with high precision capacitors that exhibit a capacitance that varies from the nominal capacitance by 5% or less. In at least one standard value embodiment, a representative value of capacitor C28 is approximately 0.068 µF, and a representative value of capacitor C33 is approximately 0.22 µF. Operational amplifier U23A is illustrated in FIG. 4 powered by supply voltages +VS2 and −VS2, which may refer to +/−2.75 V supply signals whereas analog switch U20 is illustrated powered by supply voltages +/−VS1, which may refer to +/−8 V signals.

Table 3 summarizes the gain-bandwidth configurations of second filter stage 124. While both configurations provide unity DC gain, the LP configuration constitutes a complex pole pair at approximately 10 Hz, while the WP configuration constitutes a complex pole pair at approximately 1 kHz.

| SECOND STAGE GAIN AND BANDWIDTH | | | |
|---|---|---|---|
| BANDWIDTH STATE | SWITCH U20 | DC GAIN (dB) | POLE FREQUENCY (Hz) |
| High | CLOSED | 0 | 1000 |
| Low | OPEN | 0 | 10 |

The filtered signal node 440 provides an input, through resistor R81, to an inverting input of operational amplifier U23B while resistor R83 provides a feedback path from an output terminal of operational amplifier U23B to the inverting input. The non-inverting input of operational amplifier U23B is illustrated tied to ground through resistor R85. The resistors R81 and R83 illustrated in FIG. 4 may have the same or substantially the same resistance. In at least one embodiment, resistors R81 and R83 are high precision resistors having resistances specified to vary from their nominal values by 0.1% or less. By employing precisely matched resistors, operational amplifier U23B functions as an highly accurate voltage inverter with unity gain to produce a voltage at node 450, to which the output terminal of operational amplifier U23B connects, equal in magnitude and opposite in polarity to the voltage at filtered signal node 440, thereby producing a differential signal from the unipolar signal at filtered signal node 440. In at least one standard value embodiment, a representative value of resistors R81 and R83 is approximately 20.0 KΩ, and a representative value of resistor R85 is approximately 10.0 KΩ.

The differential voltage formed between filtered signal node 440 and node 450 provides a differential voltage input to an RC circuit 126 that includes a resistor R79 connected between filtered signal node 440 and a +VIN input of analog-to-digital (ADC) U24, which serves as the ADC 130 illustrated in FIG. 1, and resistor R84 connected between node 450 and a −VIN input of ADC U24, as well as a resistor R82 and capacitor C34 connected in parallel between the +VIN and −VIN inputs of ADC U24. A representative gain of RC circuit 126 is approximately −0.2 dB at all frequencies of interest.

The ADC U24 illustrated in FIG. 4 is powered by +/−VS3 supply voltages, receives a system clock signal SCLK and a first clock signal CLK1, and produces a serial digital output signal Dout. In at least one embodiment, ADC U24 is a low power, 24-bit, 20 kHz ADC configured to receive a differential input signal and to operate from a single DC voltage supply signal. U24 may be configured to operate from a single supply signal that is level shifted or otherwise converted to provide the +/−VS3 supply signals depicted in FIG. 4. In at least one embodiment, a 5 V supply signal (not depicted) is converted to a +2.5 signal and a −2.5 V signal that are provided to U24 as its +VS3 and −VS3 supply voltages.

What is claimed:

1. A digital multimeter, comprising:
   a primary input node for receiving a primary signal;
   a multi mega-ohm input resistor coupled between the primary input node and a summing node;
   a variable gain, variable bandwidth input buffer comprising:
      an operational amplifier circuit, coupled between the summing node and a first stage output node; and
      a variable gain, variable bandwidth feedback circuit, coupled between the first stage output node and the summing node; and
   wherein:
      an input impedance of the multimeter is:
      substantially independent of a gain and bandwidth of the input buffer; and
      substantially equal to a resistance of the multi mega-ohm input resistor; and
   the feedback circuit includes:
      an AC-rejecting configuration for filtering a small amplitude DC component of a particular primary signal that further includes a large amplitude AC component; and
      at least one feedback path, coupled between the summing node and the first stage output node, comprising an impedance element in series with a feedback path switch, wherein a voltage across the feedback path switch is substantially 0 V, independent of whether the feedback path switch is open or closed.

2. The digital multimeter of claim 1, wherein a resistance of the input resistor is greater than or equal to 100 MΩ.

3. The digital multimeter of claim 2, wherein the input resistor comprises a set of ten input resistors in series, wherein each of the ten input resistors has a resistance of approximately 10 MΩ.

4. The digital multimeter of claim 1, wherein the feedback circuit includes:
   a plurality of selectable feedback paths, wherein each of the selectable feedback paths includes a configuration input configured to control the feedback path switch to couple the impedance element to the summing node.

5. The digital multimeter of claim 4, wherein the feedback circuit includes:
   a fixed feedback path connected between the summing node and the first stage output node.

6. The digital multimeter of claim 5, wherein the feedback circuit is configured to provide a plurality of gain-bandwidth configurations including:
   a high gain, wideband configuration;
   a high gain, low pass configuration;
   a low gain, wideband configuration; and
   a low gain, low pass configuration.

7. The digital multimeter of claim 6, wherein a DC gain of each of the high gain configurations is less than unity.

8. The digital multimeter of claim 7, wherein a DC gain of each of the high gain configurations is approximately −6 dB and wherein a DC gain of each of the low gain configurations is approximately −40 dB.

9. The digital multimeter of claim 7, wherein a bandwidth of each of the wideband configurations is approximately 1 kHz and wherein a bandwidth of each of the low pass configurations is about 10 Hz.

10. The digital multimeter of claim 1, further comprising:
    a shunt input node for receiving a shunt signal;
    a shunt input resistor coupled between the shunt input node and a shunt summing node;
    a variable gain, variable bandwidth shunt input buffer comprising:
       an operational amplifier circuit, coupled between the shunt summing node and a shunt stage output node; and
       a variable gain, variable bandwidth feedback circuit, coupled between the shunt stage output node and the shunt summing node; and
    wherein:
       an input impedance of the shunt input node is:
       substantially independent of the gain and bandwidth of the shunt input buffer; and
       substantially equal to a resistance of the shunt input resistor.

11. The digital multimeter of claim 10, wherein the feedback circuit of the shunt input buffer is configured to provide a plurality of gain-bandwidth configurations including:
    an amplifying gain, wideband configuration; and
    an amplifying gain, low pass configuration.

12. The digital multimeter of claim 11, wherein a DC gain of each amplifying gain configuration is approximately 14 dB.

13. The digital multimeter of claim 11, wherein a bandwidth of each wideband configuration is approximately 1 kHz and wherein a bandwidth of each low pass configuration is approximately 10 Hz.

14. The digital multimeter of claim 10, further comprising:
    a second stage comprising a variable bandwidth filter; and
    a second stage switch configured to connect either the primary stage output or the shunt stage output to a second stage output.

15. The digital multimeter of claim 14, wherein a DC gain of the second stage is approximately 1 and wherein a bandwidth of the second stage is selected from a wideband bandwidth and a low pass bandwidth.

16. The digital multimeter of claim 15, wherein the wideband bandwidth is approximately 1 kHz and the low pass bandwidth is approximately 10 Hz.

17. The digital multimeter of claim 16, wherein the second stage includes an impedance switch configured to alter an impedance of the variable bandwidth filter in accordance with a second stage input signal.

18. The digital multimeter of claim 17, further comprising:
    a differential signal circuit configured to receive an output of the second stage and produce a differential signal comprising the output of the second stage and a signal equal in magnitude and opposite in polarity to the output of the second stage.

19. The digital multimeter of claim 18, wherein the differential signal circuit includes an operational amplifier and a pair of matched resistors, wherein a first matched resistor connects the output of the second stage to an inverting input of the operational amplifier and wherein the second matched resistor connects an output of the operational amplifier and the inverting input.

20. A digital multimeter, comprising:
a primary input node for receiving a primary signal;
a multi mega-ohm input resistor coupled between the primary input node and a summing node;
a variable gain, variable bandwidth input buffer comprising:
   an operational amplifier circuit, coupled between the summing node and a first stage output node; and
   a variable gain, variable bandwidth feedback circuit, coupled between the first stage output node and the summing node;
wherein the feedback circuit is configured to provide a plurality of gain-bandwidth configurations including:
   a high gain, wideband configuration;
   a high gain, low pass configuration;
   a low gain, wideband configuration; and
   a low gain, low pass configuration; and
wherein:
   an input impedance of the multimeter is:
   substantially independent of the gain and bandwidth of the input buffer; and
   substantially equal to a resistance of the multi mega-ohm input resistor.

21. The digital multimeter of claim 20, wherein a bandwidth of the wideband configurations is approximately 1 kHz and wherein a bandwidth of the low pass configurations is about 10 Hz.

22. The digital multimeter of claim 21, wherein a DC gain of the high gain configurations is approximately −6 dB and wherein a DC gain of the low gain configurations approximately is approximately −40 dB.

23. The digital multimeter of claim 21, wherein the feedback circuit includes:
one or more feedback paths, coupled between the summing node and the first stage output node, wherein each of the one or more feedback paths includes an impedance element in series with a feedback path switch.

24. The digital multimeter of claim 23, wherein each feedback path switch is configured wherein a voltage across the feedback path switch is substantially 0 V, independent of whether the feedback path switch is open or closed.

* * * * *